(12) United States Patent
Liu et al.

(10) Patent No.: US 6,372,251 B2
(45) Date of Patent: *Apr. 16, 2002

(54) FORMULATIONS COMPRISING LIPID-REGULATING AGENTS

(75) Inventors: Rong Ron Liu, Gurnee; Qinghai Pan, Lake Bluff; Pawan Hansrani, Buffalo Grove, all of IL (US)

(73) Assignee: Abbott Laboratories, Abbott Park, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/330,589

(22) Filed: Jun. 11, 1999

(51) Int. Cl.[7] .............. A61K 9/00; A61K 9/48; A61K 9/64; A01N 25/34; A01N 25/08

(52) U.S. Cl. .............. 424/451; 424/400; 424/408; 424/409; 424/456; 514/960; 514/962

(58) Field of Search .............. 424/400, 408, 424/409, 451, 456; 514/960, 962

(56) References Cited

U.S. PATENT DOCUMENTS

| | | |
|---|---|---|
| 4,058,552 A | 11/1977 | Mieville |
| 4,739,101 A | 4/1988 | Bourgogne et al. |
| 4,800,079 A | 1/1989 | Boyer |
| 4,895,726 A * | 1/1990 | Curtet et al. ............ 424/456 |
| 4,925,676 A | 5/1990 | Ghebre-Sellassie et al. |
| 4,927,639 A | 5/1990 | Ghebre-Sellassie et al. |
| 4,957,746 A | 9/1990 | Valducci |
| 4,961,890 A | 10/1990 | Boyer |
| 5,030,447 A | 7/1991 | Joshi et al. |
| 5,180,589 A | 1/1993 | Joshi et al. |

(List continued on next page.)

FOREIGN PATENT DOCUMENTS

| | | |
|---|---|---|
| EP | 0793958 | 2/1997 |
| EP | 0 998 927 A1 | 10/1999 |
| GB | 1 590 864 | 6/1981 |
| WO | 8201649 | 5/1982 |
| WO | WO 92/10996 | 7/1992 |
| WO | WO 95/24893 | 9/1995 |
| WO | WO 98/15264 | 4/1998 |
| WO | 99/29300 | 6/1999 |
| WO | WO 99/36060 | 7/1999 |
| WO | 99/36060 | 7/1999 |
| WO | 00/37057 | 6/2000 |

OTHER PUBLICATIONS

Ming–Thau Sheu et al., Characterization and Dissolution of Fenofibrate Solid Dispersion Systems, *International Journal of Pharmaceutics*, (1994), vol. 103, pp. 137–146.

G. F. Palmieri et al., Characterization and Dissolution Studies of PEG 4000/Fenofibrate Solid Dispersions, *S.T.P. Pharma Sciences*, (1996), pp. 188–194.

A. Ben–Amor et al., Augmentation De La Biodisponibilite D'Un Agent Hypolipemiant Par Incorporation Dans Une Gelule A Contenu Liquide, Laboratoire de Pharmacie Galenique, Section de Pharmacie, Universite de Geneve, Sciences II, 30 Quai Ernest Ansermet, 12111 Geneve 4, Suisse.

Primary Examiner—Thurman K. Page
Assistant Examiner—S. Tran
(74) Attorney, Agent, or Firm—Rockey, Milnamow & Katz, Ltd.

(57) ABSTRACT

The present invention is directed to a semi-solid formulation comprising a lipid-regulating agent. Said formulation is prepared by solubilizing said lipid-regulating agent in one or more liquid components to form a clear liquid solution, then solidifying said solution by adding one or more solid or semi-solid components to said solution to form a semi-solid formulation. Said formulation can melt or dissolve upon mixing with a bulk aqueous medium. The resulting formulation results in an increase in drug solubility and oral bioavailability, and an improved dissolution rate.

9 Claims, 2 Drawing Sheets

U.S. PATENT DOCUMENTS

| | | | |
|---|---|---|---|
| 5,380,745 A | * 1/1995 | Uomoto et al. | 514/410 |
| 5,545,628 A | 8/1996 | Deboeck et al. | |
| 5,645,856 A | 7/1997 | Lacy et al. | |
| 5,798,375 A | * 8/1998 | Tsujita et al. | 514/369 |
| 5,807,834 A | 9/1998 | Morehouse | |
| 5,827,536 A | 10/1998 | Laruelle | |
| 5,880,148 A | 3/1999 | Edgar et al. | |
| 6,180,138 B1 | 1/2001 | Engh et al. | |

* cited by examiner

Mean(±SEM, n=6) Plasma Concentrations of Fenofibric Acid after a 67 mg Dose of Fenofibrate in Fasted Dogs

FORMULATIONS COMPRISING LIPID-REGULATING AGENTS

FIELD OF THE INVENTION

The present invention relates to novel formulations comprising lipid-regulating agents.

BACKGROUND OF THE INVENTION

2-[4-(4-chlorobenzoyl)phenoxy]-2-methyl-propanoic acid, 1-methylethylester, also known as fenofibrate, is representative of a broad class of compounds having pharmaceutical utility as lipid regulating agents. More specifically, this compound is part of a lipid-regulating agent class of compounds commonly known as fibrates, and is disclosed in U.S. Pat. No. 4,058,552.

Fenofibrate has been prepared in several different formulations, c.f., U.S. Pat. Nos. 4,800,079 and 4,895,726. U.S. Pat. No. 4,895,726 discloses a co-micronized formulation of fenofibrate and a solid surfactant.

U.S. Pat. No. 4,961,890 discloses a process for preparing a controlled release formulation containing fenofibrate in an intermediate layer in the form of crystalline microparticles included within pores of an inert matrix. The formulation is prepared by a process involving the sequential steps of dampening said inert core with a solution based on said binder, then projecting said fenofibrate microparticles in a single layer onto said dampened core, and thereafter drying, before said solution based on said binder dissolves said fenofibrate microparticles, and repeating said three steps in sequence until said intermediate layer is formed.

European Patent Application No. EP0793958A2 discloses a process for producing a fenofibrate solid dosage form utilizing fenofibrate, a surface active agent and polyvinyl pyrrolidone in which the fenofibrate particles are mixed with a polyvinyl pyrrolidone solution. The thus obtained mixture is granulated with an aqueous solution of one or more surface active agents, and the granulate thus produced is dried.

PCT Publication No. WO 82/01649 discloses a fenofibrate formulation having granules that are comprised of a neutral core that is a mixture of saccharose and starch. The neutral core is covered with a first layer of fenofibrate, admixed with an excipient and with a second microporous outer layer of an edible polymer.

U.S. Pat. No. 5,645,856 describes the use of a carrier for hydrophobic drugs, including fenofibrate, and pharmaceutical compositions based thereon. The carrier comprises a digestible oil and a pharmaceutically-acceptable surfactant component for dispersing the oil in vivo upon administration of the carrier, which comprises a hydrophilic surfactant, said surfactant component being such as not to substantially inhibit the in vivo lipolysis of the digestible oil.

Gemfibrozil is another member of the fibrate class of lipid-regulating agents. U.S. Pat. No. 4,927,639 discloses a disintegratable formulation of gemfibrozil providing both immediate and sustained release, comprising a tablet compressed from a mixture of a first and second granulation, and a disintegration excipient operable to effect partial or complete disintegration in the stomach. The first granulation comprises finely divided particles of pure gemfibrozil granulated with at least one cellulose derivative, and the second granulation comprises finely divided particles of pure gemfibrozil granulated with a pharmaceutically-acceptable water soluble or insoluble polymer which are then uniformly coated with a pharmaceutically-acceptable (meth)acylate copolymer prior to admixture with the first granulation. The first and second granulations are present in the final composition in a ratio of from about 10:1 to about 1:10.

U.S. Pat. No. 4,925,676 discloses a disintegratable gemfibrozil tablet providing both immediate and enteric release, which is compressed from a mixture of a first granulation of gemfibrozil with at least one acid-disintegratable binder, and a second granulation formed from the first granulation, but regranulated or coated with an alkali-disintegratable formulation of at least one substantially alkali-soluble and substantially acid-insoluble polymer.

Another class of lipid-regulating agents are commonly known as statins, of which pravastatin and atorvastatin are members. U.S. Pat. Nos. 5,030,447 and 5,180,589 describe stable pharmaceutical compositions, which when dispersed in water have a pH of at least 9, and include a medicament which is sensitive to a low pH environment, such as pravastatin, one or more fillers such as lactose and/or microcrystalline cellulose, one or more binders, such as microcrystalline cellulose (dry binder) or polyvinylpyrrolidone (wet binder), one or more disintegrating agents such as croscarmellose sodium, one or more lubricants such as magnesium stearate and one or more basifying agents such as magnesium oxide.

It is an object of the present invention to provide formulations of lipid-regulating agents having enhanced bioavailability when compared to commercially available formulations.

SUMMARY OF THE INVENTION

The present invention is directed to a semi-solid formulation comprising a lipid-regulating agent, a liquid component, and a solid or semi-solid component.

Said formulation is prepared by solubilizing said lipid-regulating agent in one or more liquid components to form a clear liquid solution, then solidifying said solution by adding one or more solid or semi-solid components to said solution to form a semi-solid formulation. Said formulation can melt or dissolve upon mixing with a bulk aqueous medium. The resulting formulation results in an increase in drug solubility and oral bioavailability, and an improved dissolution rate.

The formulation may be administered directly, diluted into an appropriate vehicle for administration, encapsulated into soft or hard gelatin capsules for administration, or administered by other means obvious to those skilled in the art.

DETAILED DESCRIPTION OF THE INVENTION

Figure 1:
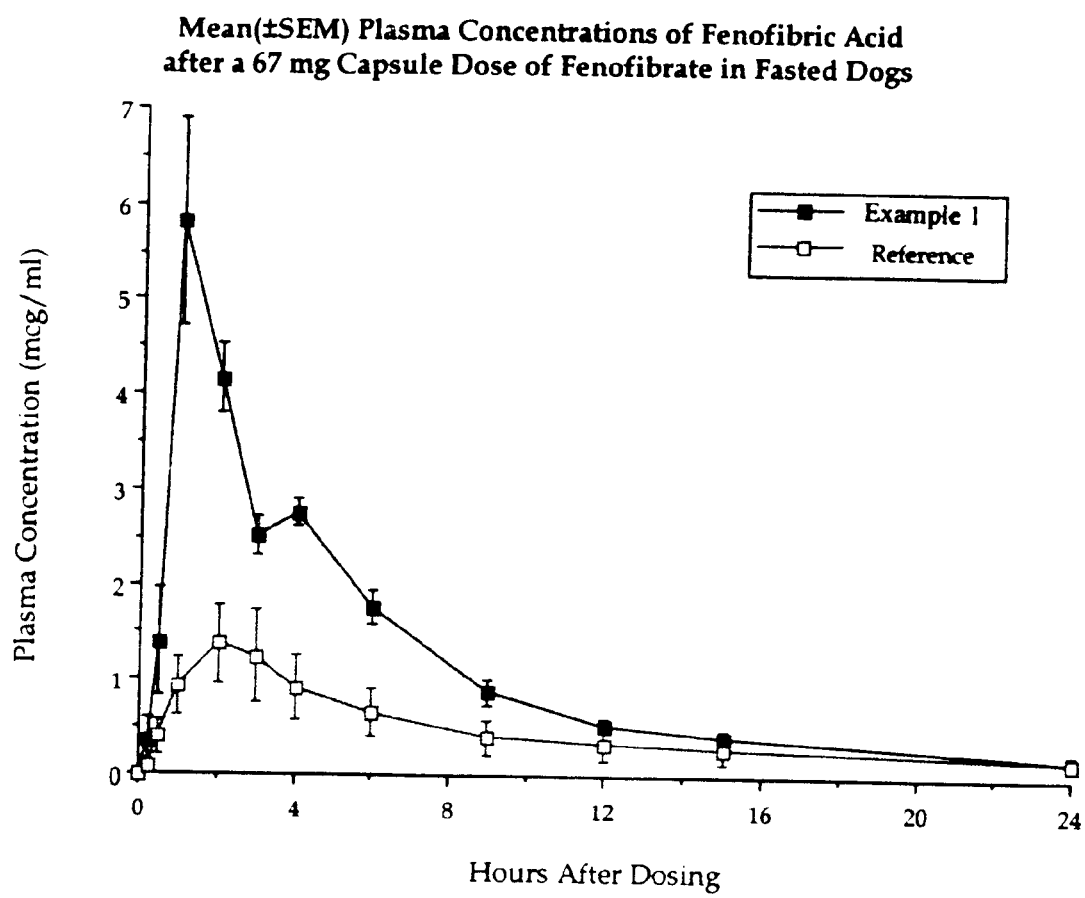
FIGS. 1 and 2 are graphs showing the plasma concentration in fasted dogs of the formulation of Example 1 and 2, respectively, and a commercial, reference compound.

The bulk lipid-regulating agent may be prepared by any available method, as for example the compound fenofibrate may be prepared by the procedure disclosed in U.S. Pat. No. 4,058,552, or the procedure disclosed in U.S. Pat. No. 4,739,101, both herein incorporated by reference.

The composition comprising the lipid-regulating agent is prepared by solubilizing said lipid-regulating agent in one or more liquid components to form a clear liquid solution, then solidifying said solution by adding one or more solid or semi-solid components to said solution to form a semi-solid formulation. Said formulation can melt or dissolve upon mixing with a bulk aqueous-medium.

The delivery system of the present invention results in increased solubility and bioavailability, and improved dissolution rate of the lipid-regulating agent.

The selection of liquid components is based on the component's ability to solubilize fenofibrate. Suitable liquid components thus include, for example, any pharmaceutically-acceptable liquid surfactants, solvents and oils.

Pharmaceutically-acceptable solvents include oily or non-aqueous solvents, for example, acetylated monoglycerides, propylene glycol fatty acid esters, including but not limited to propylene glycol dicaprylate/dicaprate, propylene glycol laurate, propylene glycol dicaprylate, and propylene glycol mono and dicaprylate; and unsaturated polyglycolysed glycerides, for example, Labrafil M 2125CS Gattefosse. Preferred acetylated monoglycerides include, for example, Myvacet 9-08, Myvacet 9-45 and Myverol 18-92 (Eastman Chemicals); Lauroglycol, a propylene glycol monolaurate (Gattefosse); and Capmul PG 8, a propylene glycol mono and dicaprylate available from Abitec.

Other solvents include, for example, pharmaceutically-acceptable alcohols such as, for example, propylene glycol; ethanol; transcutol (Gattefosse); glycerol; and polyethylene glycol 200, polyethylene glycol 300, and polyethylene glycol 400 (Union Carbide).

Other solvents include, for example, pharmaceutically acceptable oils such as, for example, mineral oil or a vegetable oil including, safflower oil, olive oil, fractionated coconut oil, for example, mixed triglycerides with caprylic acid and capric acid (Miglyol 812, Huls).

Pharmaceutically-acceptable surfactants include non-ionic surfactants such as mono fatty acid esters of polyoxyethylene sorbitan, for example, polyoxyethylene (20) sorbitan monooleate (Tween 80), polyoxyethylene (20) sorbitan monostearate (Tween 60), polyoxyethylene (20) sorbitan monolaurate (Tween 20) (Sigma); anionic surfactants such as, for example, sodium lauryl sulfate; polyoxyethylene castor oil derivatives, for example polyoxyethyleneglycerol triiricinoleate or polyoxyl 35 castor oil (Cremophor EL, BASF); and Vitamin E TPGS (d-alpha-tocopheryl polyethylene glycol 1000 succinate).

The solid or semi-solid component primarily functions as a solidifying agent, however, depending upon the characteristics of such component, such component may also assist as a solubilizer. Examples of such components include polypropylene glycol; polyethylene glycol (for example polyethylene glycol 1450, polyethylene glycol 3350, polyethylene glycol 6000, and the like (Union Carbide); polyoxyethylene castor oil derivatives, for example polyoxyethylene glycerol tricinoleate or polyoxyl 35 castor oil (Cremophor EL, BASF), polyoxyethylene glycerol oxystearate (Cremophor RH 40 (polyethylene glycol 40 hydrogenated castor oil) or Cremophor RH 60 (polyethyleneglycol 60 hydrogenated castor oil), BASF); saturated polyglycolized glycerides, for example, Gelucire 35/10, Gelucire 44/14 or Gelucire 53/10 and the like Gattefosse); polyethylene polypropylene glycols (Poloxamer 68 and Poloxamer 127 (BASF); Vitamin E TPGS (d-alpha-tocopheryl polyethylene glycol 1000 succinate, Eastman Chemical).

Other pharmaceutically-acceptable excipients may be added to the formulation prior to forming the desired final product. Suitable excipients include, for example, antioxidants (for example, ascorbic acid, BHA (butylated hydroxyanisole), and vitamin E.

The resulting composition comprising the lipid-regulating agent may be dosed directly for oral administration, diluted into an appropriate vehicle for oral administration, filled into soft or hard capsules for oral administration, or delivered by some other means obvious to those skilled in the art. The said liquid can be used to improve the oral bioavailability, and increase the half-life and solubility of said lipid-regulating agent.

The invention will be understood more clearly from the following non-limiting representative examples:

EXAMPLE 1

Myvacet 9-08 (Eastman Chemical) (402 mg) was mixed with propylene glycol laurate (Gattefosse) (67 mg). To this solution was added fenofibrate (Sigma)(67 mg) and the resulting mixture was mixed well until the fenofibrate dissolved. The resulting solution was heated to about 45–50° C. To the solution was added Vitamin E TPGS (Eastman Chemical) (134 mg) and the resulting mixture was stirred until a clear solution obtained. The resulting solution (670 mg) was filled into hard gelatin capsules while the solution was still warm and in a liquid state. Each capsule contained 67 mg of fenofibrate.

EXAMPLE 2

Capmul PG-8 (Abitec) (6.75 g) was added to a scintillation vial. Fenofibrate (Sigma) (1.0 g) was then added to the vial and mixed until it was completely dissolved. To this solution was added Cremophor RH 40 (BASF) (2.0 gm). The resulting solution was heated to about 45–50° C. and mixed until a clear solution was obtained. To this solution was added polyethylene glycol 3350 (Union Carbide) (0.25 g) and the resulting mixture was stirred until a clear solution was obtained. The resulting solution (0.67 g) was filled into hard gelatin capsules while the solution was still warm and in a liquid state. Each capsule contained 67 mg of fenofibrate.

EXAMPLE 3

| | |
|---|---|
| Pravastatin | 1.0 g |
| Myvacet 9-08 | 6.0 g |
| Propylene glycol Laurate | 1.0 g |
| Vitamin E TPGS | 2.0 g |

Add Myvacet 9-08 in a scintillation vial. Add propylene glycol laurate and mix until uniform. Add the pravastatin and mix until uniformly dispersed. Heat the solution to approximately 45–50° C. and add Vitamin E TPGS and mix until uniformly dispersed. Fill an amount of the pre-mix into capsules, sufficient to deliver the desired dose.

EXAMPLE 4

Figure 2:
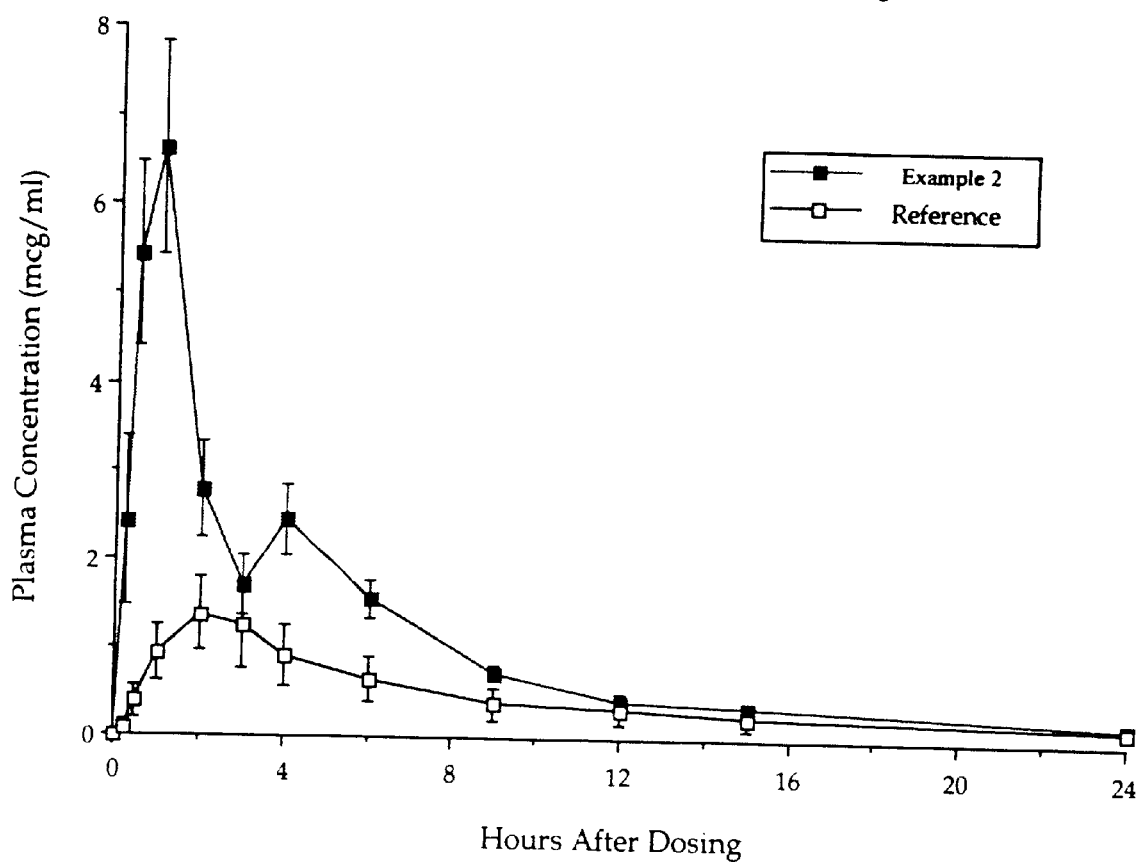

Capsules prepared by the process described in Examples 1 and 2 and from a commercial fenofibrate composition, Lipanthyl 67M (Groupe Fournier) (Reference), were administered to a group of dogs at a dose of 67 mg fenofibrate/dog (one capsule/dog). The plasma concentrations of fenofibric acid were determined by HPLC. Concentrations were normalized to a 6.7 mg/kg dose in each dog. FIGS. 1 and 2 presents the resulting data in graph form. The results provided as mean±SD, n=6, were as follows:

FIG. 1
Lipanthyl 67M (Reference):
Cmax=1.88±0.97 mcg/ml
Tmax=1.6±0.9 hr
$t_{1/2}$=4.5 hr
AUC (0–24)=11.08±9.42 mcg·hr/ml
Capsule of Example 1
Cmax=6.60±1.60 mcg/ml
Tmax=1.3±0.5 hr
$t_{1/2}$=4.4 hr
AUC (0–24)=27.68±5.62 mcg·hr/ml
FIG. 2
Lipanthyl 67M (Reference)
Cmax=1.88±0.97 mcg/ml
Tmax=1.6±0.9 hr
$t_{1/2}$=4.5 hr
AUC (0–24)=11.08±9.42 mcg·hr/ml
Capsule of Example 2
Cmax=7.74±2.27 mcg/ml
Tmax=0.7±0.3 hr
$t_{1/2}$=7.5 hr
AUC (0–24)=26.27±8.11 mcg·hr/ml

What is claimed is:

1. A composition consisting essentially of a semi-solid formulation of a fibrate and one or more liquid components in solution, and one or more solid or semi-solid components;
wherein said one or more solid or semi-solid components is a semi-solid pharmaceutical excipient or a solid pharmaceutical excipient selected from the group consisting of polyethylene glycol, polyoxyethylene castor oil derivatives, polyoxyethylene glycerol oxystearate, saturated polyglycolized glycerides, polyethylene polypropylene glycols and d-alpha-tocopheryl polyethylene glycol 1000 succinate.

2. A composition of claim 1 wherein the fibrate is fenofibrate.

3. A composition of claim 1 wherein at least one or more of said liquid components is an oily or non-aqueous solvent selected from the group consisting of acetylated monoglycerides, propylene glycol fatty acid esters, and unsaturated polyglycolysed glycerides.

4. A composition of claim 1 wherein one or more of said liquid components is a non-ionic surfactant selected from the group consisting of mono fatty acid esters of polyoxyethylene sorbitan, anionic surfactants, polyoxyethylene castor oil derivatives, and d-alpha-tocopheryl polyethylene glycol 1000 succinate.

5. A delivery system comprising a composition of claim 1.

6. A delivery system of claim 5 wherein said delivery system is a capsule.

7. A method of treating hyperlipidemia comprising the step of administering a therapeutically-effective amount of a composition of claim 1 to a patient.

8. A method of treating hyperlipidemia comprising the step of administering a therapeutically-effective amount of a composition of claim 3 to a patient.

9. A method of treating hyperlipidemia comprising the step of administering a therapeutically-effective amount of a composition of claim 6 to a patient.

* * * * *